(12) United States Patent
Klimowicz et al.

(10) Patent No.: US 6,845,770 B2
(45) Date of Patent: Jan. 25, 2005

(54) SYSTEMS AND METHODS FOR CLEARING AEROSOLS FROM THE EFFECTIVE ANATOMIC DEAD SPACE

(75) Inventors: Michael A. Klimowicz, Escondido, CA (US); James B. Fink, San Mateo, CA (US)

(73) Assignee: Aerogen, Inc., Mountain View, CA (US)

( * ) Notice: Subject to any disclaimer, the term of this patent is extended or adjusted under 35 U.S.C. 154(b) by 35 days.

(21) Appl. No.: 10/345,621

(22) Filed: Jan. 15, 2003

(65) Prior Publication Data

US 2003/0136400 A1 Jul. 24, 2003

Related U.S. Application Data

(60) Provisional application No. 60/349,763, filed on Jan. 15, 2002, provisional application No. 60/349,805, filed on Jan. 15, 2002, provisional application No. 60/380,655, filed on May 14, 2002, provisional application No. 60/408,743, filed on Sep. 5, 2002, and provisional application No. 60/439,045, filed on Jan. 8, 2003.

(51) Int. Cl.$^7$ .................. A61M 11/00; A61M 11/06
(52) U.S. Cl. .................. 128/200.16; 128/200.14; 239/338; 239/102.2
(58) Field of Search .................. 128/200.14, 200.16, 128/200.21, 200.22, 200.23, 203.12, 203.26, 203.27; 239/338, 102.2

(56) References Cited

U.S. PATENT DOCUMENTS

| | | | |
|---|---|---|---|
| 3,812,854 A | | 5/1974 | Michaels et al. |
| 4,106,503 A | * | 8/1978 | Rosenthal et al. ...... 128/200.18 |
| 5,322,057 A | | 6/1994 | Raabe et al. |
| 5,392,768 A | * | 2/1995 | Johansson et al. ...... 128/200.14 |
| 5,487,378 A | | 1/1996 | Robertson et al. |
| 5,515,841 A | | 5/1996 | Robertson et al. |
| 5,515,842 A | | 5/1996 | Ramseyer et al. |
| 5,842,468 A | * | 12/1998 | Denyer et al. ......... 128/200.23 |

FOREIGN PATENT DOCUMENTS

| | | | | |
|---|---|---|---|---|
| GB | 2164569 A | * | 3/1986 | .......... A61M/11/02 |

* cited by examiner

Primary Examiner—Henry Bennett
Assistant Examiner—Mital Patel
(74) Attorney, Agent, or Firm—Townsend and Townsend and Crew LLP

(57) ABSTRACT

An aerosolization device comprises a housing having a mouthpiece, an aerosol generator, a flow sensor and a controller. The controller is configured to begin operation of the aerosol generator upon receipt of a signal from the flow sensor indicating that a threshold flow rate has been achieved by a user when inhaling a tidal breath through the mouthpiece, and to stop operation after the passage of an operation time period that is selected such that continuation of the tidal breath delivers substantially all of the aerosol to the lungs.

22 Claims, 2 Drawing Sheets

SYSTEMS AND METHODS FOR CLEARING AEROSOLS FROM THE EFFECTIVE ANATOMIC DEAD SPACE

CROSS-REFERENCES TO RELATED APPLICATIONS

This application is a continuation-in-part and claims the benefit of U.S. Provisional Patent Application Nos. 60/349,763, filed Jan. 15, 2002; 60/349,805, filed Jan. 15, 2002; 60/380,655, filed May 14, 2002; 60/408,743, filed Sep. 5, 2002; and 60/439,045, filed Jan. 8, 2003, entitled "Methods and Systems for Operating an Aerosol Generator", the complete disclosures of which are herein incorporated by reference.

BACKGROUND OF THE INVENTION

This invention relates generally to the field of aerosolization, and in particular to the aerosolization of liquids, such as drug formulations for inhalation by a user. In one specific aspect, the invention relates to the production of an aerosol using an aerosol generator, with the aerosol generator being configured to stop aerosol production at a time selected to permit the remainder of an inhaled breath to clear any inhaled aerosol from the effective anatomical dead space and move the inhaled aerosol into a targeted portion of the respiratory tract such as the lungs.

Aerosol inhalation is useful in a variety of drug delivery applications. Aerosol delivery provides numerous advantages over other drug delivery channels such as injection, ingestion and intravenous delivery. A variety of apparatus exist for aerosolizing medicaments. Merely by way of example, U.S. Pat. Nos. 5,140,740, 5,938,117, 5,586,550, 5,758,637, and 6,014,970, the complete disclosures of which are herein incorporated by reference, describe various apparatus useful in aerosolizing liquid medicaments that a user may inhale through a mouthpiece. Apparatus for aerosolizing liquid medicaments may also be incorporated into the airflow circuit of a ventilator where a ventilator is used to provide inspiratory airflow to a patient.

One factor that may be of interest with respect to inhaled aerosol drug delivery is the amount of drug reaching predetermined target areas of the respiratory tract, where the drug can be most effective, compared to the total amount of drug that is aerosolized. It is possible that a portion of aerosolized drug that is inhaled toward the end of an inspiratory breath may not reach the target tissue and may remain in untargeted portions of the respiratory tract, such as the upper respiratory tract, where it will not be effective. Thus, such region where an inhaled drug will not be effective can be said to comprise the effective anatomical dead space of the respiratory tract, because the inhaled drug will not reach the targeted portions of the respiratory tract and will be exhaled without having been utilized by the body of the user.

Thus, it is possible that a user may receive a smaller amount of drug than a chosen aerosol dose. This could result in a user being under-medicated or in the calculation of an inappropriate dose amount. In addition, such lost amounts of drug can adversely impact on the financial cost of a particular therapy. Further, such unused drug, when it is exhaled into the ambient air in what may be referred to as a puff, can be inhaled by other people in the vicinity of the user. Such individuals may be affected by inhaling what could be referred to as second-hand medication.

Accordingly, there is a need for systems and methods to reduce the amount of aerosolized drug that is unused, because it remains in the effective anatomical dead space, by clearing such aerosol from dead space in the respiratory tract so that a greater portion of the aerosolized drug reaches a chosen target region.

BRIEF SUMMARY OF THE INVENTION

The invention provides techniques and devices that are designed to facilitate the transfer of an aerosol to the lungs. The techniques and devices are particularly useful in applications where an aerosol is generated on demand. This may occur, for example, when a user inhales from a mouthpiece to cause production of the aerosol. As the user continues to inhale, the aerosol is delivered to the lungs. In some cases, the last portion of the generated aerosol may not reach the lungs. This last portion of the aerosol simply fills a so-called dead space between the exit of the inhaler mouthpiece and the entrance to targeted portion of the respiratory tract, such as the lung.

The invention provides exemplary aerosolization devices and methods for delivering an aerosol to the lungs. In one embodiment, an aerosolization device comprises a housing having a mouthpiece, an aerosol generator disposed in the housing, a flow sensor or pressure sensor, and a controller to control operation of the aerosol generator. The controller is configured to begin operation of the aerosol generator upon receipt of a signal from the sensor indicating that a threshold flow rate has been achieved by a user inhaling a breath through the mouthpiece. The controller is further configured to stop operation of the aerosol generator after passage of an operation time period that is selected such that continuation of the inspiration of the breath delivers substantially all of the produced aerosol to a predetermined region of the respiratory tract, such as the user's lungs.

In this way, aerosol production begins when the user has achieved an acceptable inspiratory flow rate. Further, aerosol production is stopped during the last portion of the inspiratory portion of the breath so that the remainder of the inspiratory breath, which is absent aerosolized drug, and thus may be referred to as a chaser, moves the aerosol through the patient's airway and into the targeted portion of the respiratory tract, such as the lungs, so that essentially no aerosol remains in the user's upper airway during inhalation.

The effective anatomical dead space volume may conveniently be defined as the volume of the respiratory tract in which a selected medication is essentially ineffective, such as the upper airway in the case of a medication targeted for the lower portions of the respiratory tract. The effective anatomic dead space may also be referred to as the effective dead space or simply as dead space.

For example, for medication targeted for the lungs and the trachea, the effective anatomical dead space may be defined by the upper airway. For medications targeted for systemic treatment, the targeted portion of the respiratory system may be what can be referred to as the deep lung, the effective anatomic dead space may be defined as the volume of the upper airway and the conducting airway that includes the trachea.

The effective dead space for a given user and a given regimen can be estimated by using easily measured anatomical measurement or criteria. For example, the average or ideal weight of a person based on height, sex and age can be used to approximate the what may be referred to at the anatomic dead space, which consists of the upper airway and the conducting airway that includes the trachea, based on a ratio of 1 cubic centimeter, or 1 milliliter, per pound of weight. If the effective anatomic dead space for a given regimen is to comprise only the upper airway portion of the anatomic dead space, this volume can be estimated, for example, as one half or on third of the anatomic dead space. Thus, for example, for applications targeted for the conductive airway and the lungs, the effective anatomic dead space will be the volume of the upper airway, which can range from about 30 cc to about 100 cc. Thus, an aerosolization device according to the present invention may be calibrated for a wide variety of users.

In one aspect, the controller includes a stored value that is an estimate of a delivery time period to essentially fill a dead space volume with generally aerosol free chase air from a tidal breath. The stored value may be used by the controller to calculate the operation time period for aerosol to be produced. The controller may include a random access memory for storing the operation time period. In an aspect of the invention, the controller may calculate and store an initialization time period. The initialization time period may be calculated as the time period during which the flow rate of inspiratory breath is above a threshold flow rate. The controller may then calculate the operation time period by subtracting the stored value from the initialization time period. In this manner, each time the user inhales, aerosol production begins when the threshold flow rate is achieved and ends after the operation time period that has already been calculated and stored in the controller. Continuation of the inhalation, now with air that is absent aerosol, which may be referred to as chaser or chase air, then moves substantially all of the aerosol into the targeted region of the respiratory tract, such as the lungs.

In one specific aspect, the aerosol generator comprises a plate having a plurality of apertures and a piezoelectric transducer that is coupled to the controller to vibrate the aperture plate. Conveniently, the aperture plate may be dome shaped in geometry and the apertures may be tapered. In another aspect, the flow sensor may be configured to produce an electrical signal that is related to the flow rate and to send the electrical signal to the controller. In this way, the aerosol generator may be actuated when a threshold signal is received.

In one exemplary method, a user inhales a tidal breath through a mouthpiece to produce a flow of air through the mouthpiece. The flow of air is sensed with the flow sensor to determine a starting time for the aerosol generator. At the starting time, the controller operates the aerosol generator during an initial portion of the breath to produce an aerosol, and then stops operation of the aerosol generator at a time selected such that continuation of the breath clears the upper airway and delivers substantially all of the produced aerosol to the lungs.

In one aspect of the invention, an inspiratory breath may conveniently begin at a time designated as T0. The aerosol generator may begin operation at a time T1 when the sensor senses that the flow produced by the inhaled breath exceeds a threshold flow rate. The aerosol generator may then be stopped before the inspiratory breath has been completed at a time T2. The inspiratory breath continues and the time at which the inspiratory flow falls below the threshold flow rate may be designated as time T3 and the time at which inhalation stops may be designated as time T4. The time period between T2 and T3 is an estimate of the time needed to move substantially all of the produced aerosol from a dead space volume and further into the respiratory tract with the continued inhalation of generally aerosol free chase air. Time T3 may be a previously measured time at which the flow produced by inhalation fell below the threshold flow rate. In one aspect, the threshold flow rate can be about 8 liters per minute. The user may take repeated breaths through the mouthpiece of the device. Each time a breath is taken, the aerosol generator starts at a new time T1 as sensed by the flow sensor and is stopped after the aerosol generation time period has expired at time T2.

The invention further provides a method for initializing an aerosolizer. According to the method, an initial breath is taken through the mouthpiece to produce a flow of air through the mouthpiece, and the flow of air is sensed with the flow sensor. The controller measures and stores an initialization time period where the inhaled breath exceeds a threshold flow rate, which can be represented as T3−T1. The controller further calculates an aerosol generator operation time period that is equal to the initialization time period minus a stored value in the controller that is an estimate of a time period to move substantially all of an aerosol produced from the aerosol generator through a dead space volume with generally aerosol free chase air from a breath. The stored value can be a percentage of the time period T3−T1 or can be a value taken from a look up table of values that represent the time during which an inspiratory flow would fill the effective dead space based on breathing criteria and anatomic estimates according to a patient's individual statistics. Thus, with such information provided in the memory of the controller, a device according to the present invention may be calibrated and used with a wide variety of patents and regimen. For example, a tidal breathing regimen may be chosen, in which a patient simply maintains a normal quiet breathing pattern. Alternatively, a chosen regimen may be a breath hold maneuver in which the patient inhales and then holds the breath for a particular interval of time before relaxing to allow exhalation. Similarly, other breath maneuvers may be used, for example, in which a user is instructed to breathe deeply or to inhale for a specific time period. In addition, a user may be on a ventilator in which air is supplied to the user's respiratory tract by a machine, either upon an attempted inhalation or automatically. Through either an initialization phase or stored or calculated values, or a combination thereof, a device or method according the present invention will determine the time for aerosolization such that the aerosol will clear the effective dead space by the remainder of the inhaled breath.

The invention provides for the measurement of the time period required to take a tidal breath or any other breath maneuver, and to estimate the time to fill the dead space volume. Once the time to fill the dead space is estimated, the inhaler device may use this information to stop aerosol production at a appropriate time on subsequent breaths so that the remaining aerosol is removed from the dead space volume by the remaining breath. Each new breath may also be tracked for any changes from the initial breath so that the controller can continually update the aerosol operation time, based on changes in the inhalation time, for subsequent breaths. In this way the system can adapt to varying breathing patterns with breath to breath updates. This results in increased aerosol delivery efficiency and thus reduces the amount of wasted drug. In addition, such operation can reduce the amount of aerosol exhaled into the environment. In this way, the amount of any of what may be referred to as second hand aerosol that may be inadvertently exhaled into the atmosphere may be reduced.

DETAILED DESCRIPTION OF THE INVENTION

Figure 1:
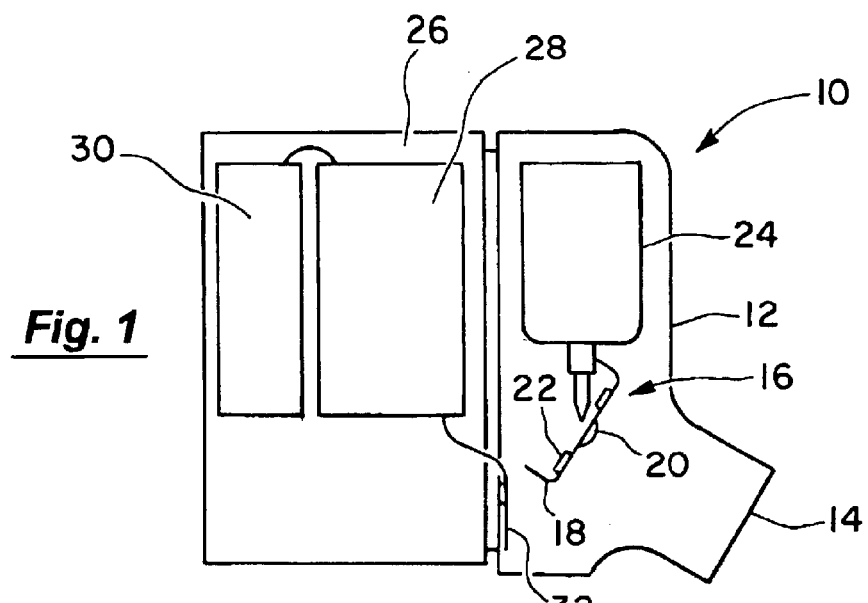
FIG. 1 is a cross sectional schematic diagram of an aerosolization device having a flow sensor according to the present invention.

The invention provides techniques and devices that are designed to facilitate the transfer of an aerosol to the lungs or other target regions of the respiratory tract. The techniques and devices are particularly useful in applications where an aerosol is generated on demand. This may occur, for example, when a user inhales from a mouthpiece to cause production of the aerosol. As the user continues to inhale, the aerosol is delivered to the lungs. In some cases, the last portion of the generated aerosol may not reach the lungs. This last portion of the aerosol simply fills a so-called dead space between the exit of the inhaler mouthpiece and the entrance to targeted portion of the respiratory tract, such as the lungs.

The invention provides exemplary aerosolization devices and methods for delivering an aerosol to the lungs. In one embodiment, an aerosolization device comprises a housing having a mouthpiece, an aerosol generator disposed in the housing, a flow sensor or pressure sensor, and a controller to control operation of the aerosol generator. The controller is configured to begin operation of the aerosol generator upon receipt of a signal from the sensor indicating that a threshold flow rate has been achieved by a user inhaling a breath through the mouthpiece. The controller is further configured to stop operation of the aerosol generator after passage of an operation time period that is selected such that continuation of the inspiration of the breath delivers substantially all of the produced aerosol to a predetermined region of the respiratory tract, such as the user's lungs.

In this way, aerosol production begins when the user has achieved an acceptable inspiratory flow rate. Further, aerosol production is stopped during the last portion of the inspiratory portion of the breath so that the remainder of the inspiratory breath, which is absent aerosolized drug, and thus may be referred to as a chaser, moves the aerosol through the patient's airway and into the targeted portion of the respiratory tract, such as the lungs, so that essentially no aerosol remains in the user's upper airway during inhalation.

In one aspect, the present invention is embodied in a system that supplies, or a method of supplying, aerosol for the entire first inhalation or for the entire first inhalation during which an inhalation is sensed, or for a fixed predetermined period of time during the first inhalation, such as, for example, the first half second of the first inspiration or the first half second of the first inspiration after an inhalation is sensed. In subsequent breaths, the aerosol is supplied according to parameters determined according to the other aerosol limiting aspects of the invention as described herein. In such system or method, the user is assured that the device is working in that a portion of aerosol is supplied with the first breath, so as to not give cause for concern to a user by an initial breath with no aerosol action by the device, while the aerosol is cleared from the effective dead space during the remainder of breaths taken by a user.

The effective anatomical dead space volume may conveniently be defined as the volume of the respiratory tract in which a selected medication is essentially ineffective, such as the upper airway in the case of a medication targeted for the lower portions of the respiratory tract. The effective anatomic dead space may also be referred to as the effective dead space or simply as dead space.

For example, for medication targeted for the deep lung through the trachea, the effective anatomical dead space may be defined by the upper airway. The upper airway may be defined, when inhalation is by mouth, as the volume from the ambient air to the tracheobronchial tree, including the mouth, pharynx and larynx. The volume between the upper airway and the first 16 generations of the airway, which may be referred to as the conducting airway, comprises the trachea, bronchus and terminal bronchioles. For medications targeted for systemic treatment, the targeted portion of the respiratory system may be what can be referred to as the deep lung, from the 17th generation of the airway to the alveoli. In this case, the effective anatomic dead space may be defined as the volume of the upper airway and the conducting airway, through the first 16 generations of the airway. This volume may be referred to as the anatomic dead space. The various portions of the respiratory tract are described in Clinical Practice in Respiratory Care, Fink & Hunt, (Lippincott, Williams & Winters, Philadelphia, Pa., 1999), the entire contents of which is hereby incorporated herein by reference.

The effective dead space for a given user and a given regimen can be estimated by using easily measured anatomical measurement or criteria. For example, the average or ideal weight of a person based on height, sex and age can be used to approximate the anatomic dead space, based on a ratio of 1 cubic centimeter, or 1 milliliter, per pound of weight. If the effective anatomic dead space for a given regimen is to comprise only the upper airway portion of the anatomic dead space, this volume can be estimated, for example, as one half or one third of the anatomic dead space. Thus, for example, for applications targeted for the conductive airway and the lungs, the effective anatomic dead space will be the volume of the upper airway, which can range from about 30 cc to about 100 cc. Thus, an aerosolization device according to the present invention may be calibrated for a wide variety of users.

In one aspect, the controller includes a stored value that is an estimate of a delivery time period to essentially fill a dead space volume with generally aerosol free chase air from a tidal breath. The stored value may be used by the controller to calculate the operation time period for aerosol to be produced. The controller may include a random access memory for storing the operation time period. In an aspect of the invention, the controller may calculate and store an initialization time period. The initialization time period may be calculated as the time period during which the flow rate of inspiratory breath is above a threshold flow rate. The controller may then calculate the operation time period by subtracting the stored value from the initialization time period. In this manner, each time the user inhales, aerosol production begins when the threshold flow rate is achieved and ends after the operation time period that has already been calculated and stored in the controller. Continuation of the inhalation, now with air that is absent aerosol, which may be referred to as chaser air, then moves substantially all of the aerosol into the targeted region of the respiratory tract, such as the lungs.

In one specific aspect, the aerosol generator comprises a plate having a plurality of apertures and a piezoelectric transducer that is coupled to the controller to vibrate the aperture plate. Conveniently, the aperture plate may be dome shaped in geometry and the apertures may be tapered. In another aspect, the flow sensor may be configured to produce an electrical signal that is related to the flow rate and to send the electrical signal to the controller. In this way, the aerosol generator may be actuated when a threshold signal is received.

In one exemplary method, a user inhales a tidal breath through a mouthpiece to produce a flow of air through the mouthpiece. The flow of air is sensed with the flow sensor to determine a starting time for the aerosol generator. At the starting time, the controller operates the aerosol generator during an initial portion of the breath to produce an aerosol, and then stops operation of the aerosol generator at a time selected such that continuation of the breath clears the upper airway and delivers substantially all of the produced aerosol to the lungs.

In one aspect of the invention, an inspiratory breath may conveniently begin at a time designated as T0. The aerosol generator may begin operation at a time T1 when the sensor senses that the flow produced by the inhaled breath exceeds a threshold flow rate. The aerosol generator may then be stopped before the inspiratory breath has been completed at a time T2. The inspiratory breath continues and the time at which the inspiratory flow falls below the threshold flow rate may be designated as time T3 and the time at which inhalation stops may be designated as time T4. The time period between T2 and T3 is an estimate of the time needed to move substantially all of the produced aerosol from a dead space volume further into the respiratory tract with the continued inhalation of generally aerosol free chase air. Time T3 may be a previously measured time at which the flow produced by inhalation fell below the threshold flow rate. In one aspect, the threshold flow rate can be about 8 liters per minute. The user may take repeated breaths through the mouthpiece of the device. Each time a breath is taken, the aerosol generator starts at a new time T1 as sensed by the flow sensor and is stopped after the aerosol generation time period has expired at time T2.

The invention further provides a method for initializing an aerosolization device or nebulizer. According to the method, an initial breath is taken through the mouthpiece to produce a flow of air through the mouthpiece, and the flow of air is sensed with the flow sensor. The controller measures and stores an initialization time period where the inhaled breath exceeds a threshold flow rate, which can be represented as T3–T1. The controller further calculates an aerosol generator operation time period that is equal to the initialization time period minus a stored value in the controller that is an estimate of a time period to move substantially all of an aerosol produced from the aerosol generator through a dead space volume with generally aerosol free chase air from a breath. The stored value can be a percentage of the time period T3–T1 or can be a value taken from a look up table of values that represent the time during which an inspiratory flow would fill the effective dead space based on breathing criteria and anatomic estimates according to a patient's individual statistics. Thus, with such information provided in the memory of the controller, a device according to the present invention may be calibrated and used with a wide variety of patents and regimen. For example, a tidal breathing regimen may be chosen, in which a patient simply maintains a normal quiet breathing pattern. Alternatively, a chosen regimen may be a breath hold maneuver in which the patient inhales and then holds the breath for a particular interval of time before relaxing to allow exhalation. Similarly, other breath maneuvers may be used, for example, in which a user is instructed to breathe deeply or to inhale for a specific time period. In addition, a user may be on a ventilator in which air is supplied to the user's respiratory tract by a machine, either upon an attempted inhalation or automatically. Through either an initialization phase or stored or calculated values, or a combination thereof, a device or method according the present invention will determine the time for aerosolization such that the aerosol will clear the effective dead space by the remainder of the inhaled breath.

It is also possible to calculate the time required to fill the effective dead space in connection with a specific regimen by bench testing with the aid of a breath simulator device and an aerosol generator device. Tubes of different lengths may alternatively be used between the aerosol generator and the breath simulator, along with a filter to catch the aerosol. The simulator is then operated to simulate a breathing pattern or regimen, and aerosol can be supplied for a fixed portion of the inhalation, each time with a tube of a different length encompassing a known volume, such as 50 ml, 100 ml or other volumes of effective dead space. It can then be observed which volumes will be cleared by the action of the breath simulator on the tube volume for a specific percentage of inhalation during which aerosol generation has been stopped. In this manner, a fixed length of time can be estimated to be, or observed as, a fixed time that would provide clearance of the effective dead space over a range of effective dead space volumes, such as, for example, turning the aerosol off at a point at which 15% of the breath follows to clear the effective dead space.

In another aspect of the invention, dead space volume can be estimated based on anatomical measurements or parameters, and different inhalation times can be entered in a table with estimated percentages of times of aerosolization shut off would be used to clear a given volume based on the length of time of the inhalation. For example, it can be estimated that for clearing an upper airway effective dead space, with an inhalation of 0.5 to 1 second, the last 33% of the breath should be without aerosol, for a 1 to 2 second inhalation, that the last 25% be without aerosol, for a 2–3 second inhalation, the last 15% should be without aerosol, and for an inhalation of over 3 seconds, the last 10% should be without aerosol. With such information incorporated into the memory of the controller, aerosol generation can be stopped with different percentages of remaining inhalation clearing the effective dead space, based on the duration of the inhalation.

The invention may be used with essentially any atomizer which atomizes a liquid medicament, such as those described in U.S. Pat. Nos. 5,140,740, 5,938,117, 5,586,550, 5,758,637, and 6,014,970, previously incorporated by reference. However, it will be appreciated that the invention is not intended to be limited to only these specific atomizers, but may be used with any atomization device where an air flow is provided through the device as just described. Further, the invention may also be used with essentially any type of ventilator that is breath actuated. Merely by way of example, one type of ventilator that may be used with the invention is described in copending U.S. application Ser. No. 09/849,194, filed May 4, 2001, the complete disclosure of which is herein incorporated by reference.

Referring now to FIG. 1, one embodiment of an aerosolization device 10 will be described. The device 10 comprises a housing 12 to hold the various components of aerosolization device 10. The housing 12 further includes a mouthpiece 14 and one or more vents (not shown) to permit air to enter into housing 12 when a user inhales from mouthpiece 14. Disposed within housing 12 is an aerosol generator 16 that comprises a cup shaped member 18 to which is coupled an aperture plate 20. An annular piezoelectric element 22 is in contact with the cup shaped member 18, so that when electrical current is supplied to piezoelectric element 22, the cup shaped member 18 vibrates, causing the aperture plate 20 to vibrate. The aperture plate 20 is dome shaped in geometry and includes a plurality of tapered apertures that narrow from the rear concave surface to the front convex surface. Exemplary aperture plates and aerosol generators that may be used in aerosolization device 10 are described in U.S. Pat. Nos. 5,140,740, 5,938,117, 5,586,550, 5,758,637, and 6,014,970, previously incorporated by reference.

Aerosolization device 10 further includes a container 24 having a supply of liquid that is to be aerosolized by aerosol generator 16. The container 24 may include a metering valve or other liquid supply system to place a metered amount of liquid onto concave rear surface of the aperture plate 20. Although not shown, a button, electrical solenoid, or the like may be employed to dispense the volume of liquid when requested by the user. Alternatively, the container 24 may be a unit dose drug ampoule, and such unit dose ampoule may be opened, for example, by tearing or piercing prior to or upon insertion into the device 10. Further, the container 24 may be supplied from another container (not shown) or a fluid tube or reservoir may be situated between the container and the aperture plate 20 to facilitate delivery of fluid to the aperture plate 20.

The device 10 includes an electronics region 26 for holding the various electrical components of aerosolization device 10. For example, the electronics region 26 may include a printed circuit board 28 which serves as a controller to control operation of the aerosol generator 16. The circuit board 28 may send an electrical signal to the piezoelectric element 22 to vibrate the aperture plate 20. The circuit board 28 may also include appropriate memory. A power supply 30, such as one or more batteries, is electrically coupled to the circuit board 28 to provide the aerosolization device 10 with power.

Figure 2:
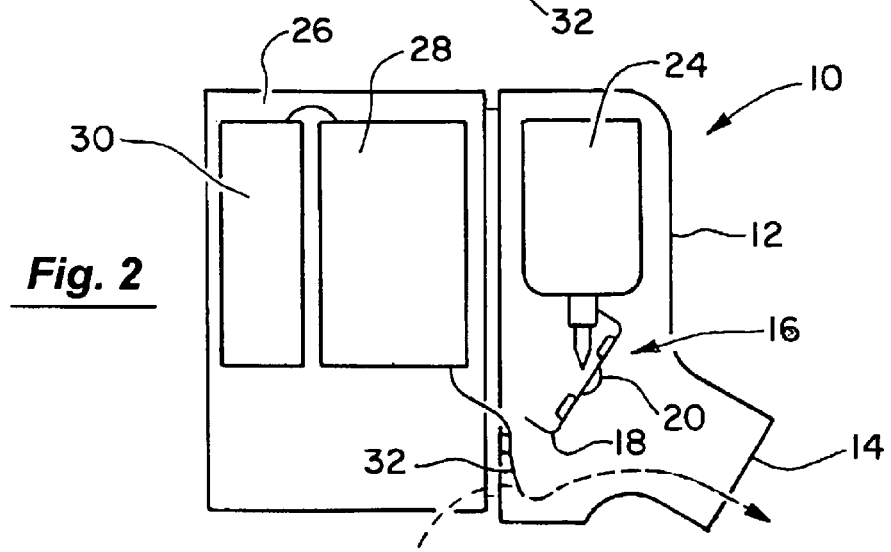
FIG. 2 illustrates the aerosolization device of FIG. 1 when air is flowing through the device to actuate the flow sensor.

The housing 12 of the aerosolization device 10 contains a flow sensor 32 that is electrically coupled to circuit board 28. The flow sensor 32 is positioned across a flow path extending between one or more inlet vents and mouthpiece 14. The flow sensor 32 is configured as a bend sensor that bends when a user inhales from mouthpiece 14 to create a flow of air through the housing 12 as shown in FIG. 2. The flow sensor 32 bends in proportion to the rate of air flowing through the housing 12. The flow sensor 32 is also configured to produce an electrical signal that is proportional to the amount of bending. The signal is transferred to the circuit board 28 which may be configured to send an electrical signal to the piezoelectric element 22 when a threshold signal, such as a voltage drop has been produced by the sensor 32. As long as the threshold voltage drop is maintained, the circuit will supply an electrical signal to the piezoelectric element 22 so that the aerosol generator 16 will aerosolize liquid provided to it. If, however, the user produces a flow rate which causes the voltage drop to fall below the threshold value, circuit board 28 will stop supplying electrical current to aerosol generator 16, thereby stopping the aerosolization process. Further, circuit board 28 may be configured to record the flow rate of air over time to measure the volume of air flowing through mouthpiece 14. In this way, circuit board 28 may be employed to determine the user's tidal volume or the volume of air the user inhales according to a given breathing regimen.

Figure 3:
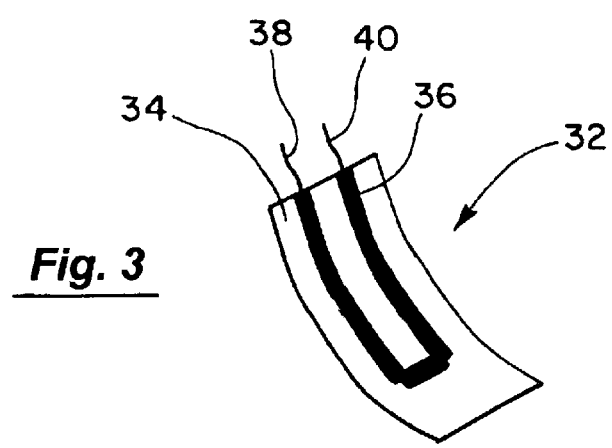
FIG. 3 is a perspective view of one embodiment of a flow sensor according to the present invention.

Referring now to FIG. 3, flow sensor 32 will be described in greater detail. Flow sensor 32 comprises a thin flexible sheet 34 having a thin layer of strain sensitive polymer 36 that is disposed on sheet 34. A pair of electrical leads 38 and 40 may be electrically coupled to polymer 36 to measure a change of voltage that is proportional to the amount of bending of sheet 34. Hence, circuit board 28 (see FIG. 1) may be electrically coupled to leads 38 and 40 and include circuitry to measure a voltage drop as the user inhales from mouthpiece 14. This information may then be employed to measure the flow rate through mouthpiece 14. In one particular embodiment, flexible sheet 34 may have width of about 5 mm, a length of about 20 mm, and a thickness of about 20 microns. Examples of sensors that may be used in aerosolization device include the Bend Sensor®, commercially available from Flexpoint Flexible Sensor Systems of Midvale, Utah. Other types of sensors that may be used include those described in U.S. Pat. No. 6,014,970, and in copending U.S. application Ser. No. 09/705,063, filed Nov. 2, 2000, incorporated herein by reference. However, it will be appreciated that the invention is not intended to be limited to only the sensors described herein. For example, the sensor may be a pressure sensor that senses a pressure drop in the housing at a predetermined pressure drop created by a user inhaling through the mouthpiece.

Figure 4:
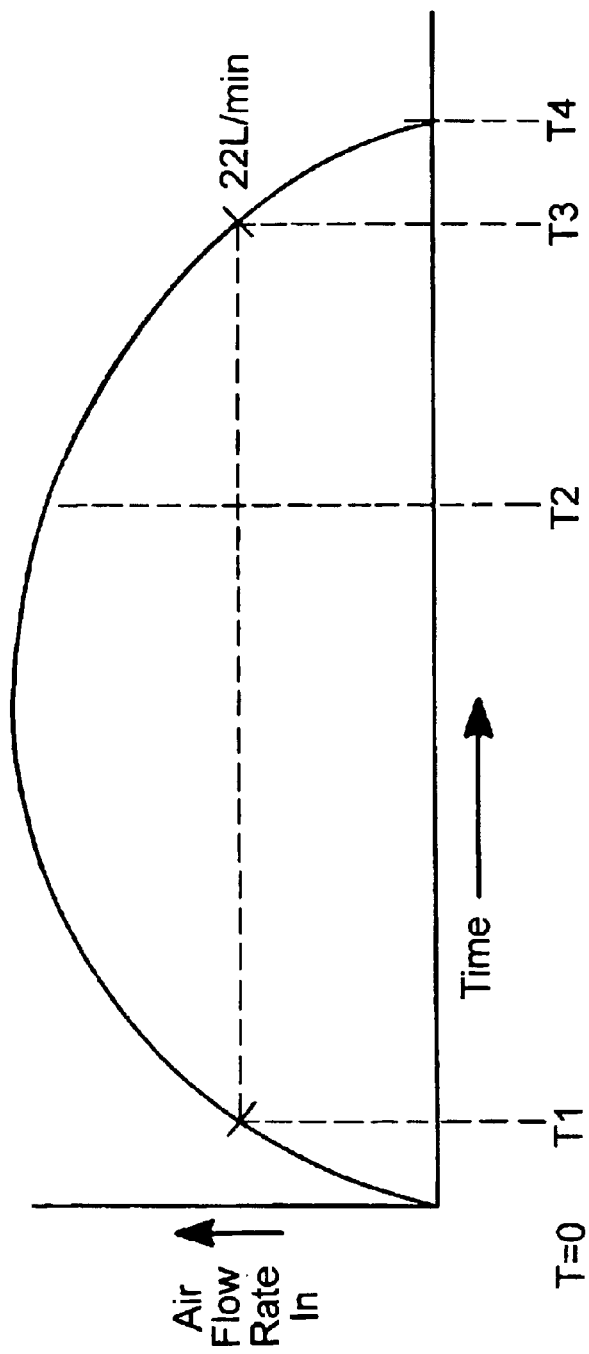
FIG. 4 illustrates a graph of the flow rate versus time when taking a breath from an inhaler and how aerosol operation time is calculated according to the present invention.

Referring now to FIG. 4, a technique for initializing and operating an inhaler, such as aerosolization device 10, will be described. To initialize the device 10, a user takes an initial breath from the mouthpiece 14. The sensor 32 senses the airflow through the housing 12 and the circuit board 28 records the flow rate over time. This is illustrated in the graph of FIG. 4. When initializing the device 10, a user may place the device 10 in an initialization mode, by operating a button or knob that sends a signal to the circuit board 28, so that the aerosol generator is not actuated.

The controller of circuit board 28 determines and stores in memory a start time T0 and end of breath time T4. Also, the controller stores in random access memory a time when the flow rate goes above a threshold flow rate, time T1 and then back below the threshold flow rate at time T3. The threshold flow rate is a rate at which the controller is configured to begin operation of aerosol generator 16. This is typically about 8 liters per minute for both time T1 and time T3. Stored in memory is an estimate of a time T2 to time T3 which is defined as an estimate of the time needed to move essentially all the aerosol from the dead space volume.

The time period from T2 to T3 may be determined from a variety of factors, such as anatomic measurements or criteria of a user, such as, for example the average or generally accepted ideal weight for a given height, sex or age. Adjustments to such estimate may be made based on individual condition of the user, such as, for example, a physical condition that reduces the volume of the respiratory tract, such as excessive secretions within the respiratory tract or swollen tissue. In addition, the controller can use information based on the sensed breathing of a user, and thus, for example, determine an average over several breaths of the time T1 and time T3 and thus the value of time T3−T1. This information can be factored into the calculation of the length of the time T3−T2 to determine when time T2 should be set. The time period of time T3−T2 may be calculated as a percentage of the time period of T3−T1. Alternatively, for a given user and regimen, the time period of time T3−T2 may be set as a constant. Any of these values may be stored in the random access memory of the device to be available for calibration, or drug delivery, for an individual user and regimen: the time from T1 to T3, 2) averaging over several prior breaths, 3) a percentage of T3−T1, 4) a fixed value and 5) a calculation to determine dead space based on a T3−T2 time period. With this information, device 10 is able to initialize itself by calculating an aerosol operation or delivery time according to the formula: (T3−T1)−(T3−T2). Further, the time T3−T1 may be monitored in subsequent breaths and changes can be factored or recalculated into the formula of (T3−T1)−(T3−T2).

Once initialized, device 10 may be placed into operational mode. As the user takes a tidal breath from mouthpiece 14, flow sensor 32 senses when the threshold flow rate has been achieved. The controller then actuates the aerosol generator to begin production of the aerosol The controller then stops operation of the aerosol generator after the passage of the aerosol operation time that was previously calculated and stored in memory as herein described. When aerosol production stops, the user continues to inhale until the end of the breath. This causes fresh air to travel through the housing and the user's airway to deliver the remaining aerosol from the dead space volume and into the targeted region of the respiratory tract, such as the deep lung. Each time the user inhales, this same process is repeated. This may be necessary, for example, when taking repeated breaths to receive a unit dose of a drug.

By delivering substantially all of the aerosol to the lungs, the efficiency and effectiveness of the inhaler is increases. Moreover, the chances of inadvertently exhaling so-called second hand aerosol are reduced.

The invention has now been described in detail for purposes of clarity of understanding. However, it would be appreciated that certain changes and modifications may be practiced within the scope of the appended claims.

What is claimed is:

1. An aerosolization device comprising:
    a housing having a mouthpiece;
    an aerosol generator disposed in the housing;
    a flow sensor; and
    a controller to control operation of the aerosol generator;
    wherein the controller is configured to begin operation of the aerosol generator upon receipt of a signal from the flow sensor indicating that a threshold flow rate has been achieved by a user when inhaling through the mouthpiece and to stop operation of the aerosol generator after passage of an operation time period that is selected such that continuation of the breath delivers substantially all of the produced aerosol to the user's lungs, and wherein the controller includes a stored value that is an estimate of a delivery time period to essentially fill a predetermined dead space volume with generally aerosol free chase air from a breath, and wherein the controller is configured to calculate the operation time period using the stored value.

2. A device as in claim 1, wherein the controller is configured to calculate and store an initialization time period that is equal to the length of time that the flow rate is above the threshold flow rate during an initialization process, and wherein the controller is further configured to calculate the operation time period by subtracting the stored value from the initialization time period.

3. A device as in claim 1, wherein the aerosol generator comprises a plate having a plurality of apertures and a piezoelectric transducer that is coupled to the controller to vibrate the aperture plate.

4. A device as in claim 3, wherein the aperture plate is dome shaped in geometry and the apertures are tapered.

5. A device as in claim 1, wherein the flow sensor is configured to produce an electrical signal that is related to the flow rate and to send the electrical signal to the controller.

6. A device as in claim 1, wherein the dead space volume is an estimate of an upper airway volume.

7. A device as in claim 1, wherein the controller includes a random access memory for storing the operation time period.

8. A device as in claim 1, further comprising a supply of liquid disposed in the housing to provide liquid to the aerosol generator.

9. A method for aerosolizing a liquid, the method comprising:
    providing an aerosolization device comprising a housing having a mouthpiece, an aerosol generator disposed in the housing, a flow sensor, and a controller to control operation of the aerosol generator;
    inhaling a tidal breath through the mouthpiece to produce a flow of air through the mouthpiece;
    sensing the flow of air with the flow sensor to determine a starting time for the aerosol generator; and
    at the starting time and with the controller, operating the aerosol generator during an initial portion of the tidal breath to produce an aerosol, and then stopping operation of the aerosol generator at a time selected such that continuation of the tidal breath delivers substantially all of the produced aerosol to the lungs, wherein T0 is defined as the commencement of the inhalation, and further comprising:
    sensing that the inhaled breath exceeds a threshold and defining the threshold time as time T1; and
    sending a signal from the controller to operate the aerosol generator at time T1.

10. A method as in claim 9, wherein the aerosol generator is stopped after expiration of an aerosol generation time period that is generally equal to a time period from time T1 to a time T3 minus a time period from a time T2 to time T3, where the time period from T2 to time T3 is an estimate of the time to move substantially all of the produced aerosol from a dead space volume with generally aerosol free chase air from the remaining tidal breath, wherein the dead space volume is a volume between the mouthpiece and the entrance to the lungs, and wherein time T3 is a previously measured time when a flow produced by a tidal breath fell below the threshold flow rate.

11. A method as in claim 9, wherein the threshold flow rate is about 8 liters per minute.

12. A method as in claim 9, further comprising inhaling another tidal breath through the mouthpiece, and beginning operation of the aerosol generator at a new time T1 as sensed by the flow sensor, and stopping operation of the aerosol generator after the aerosol generation time period has expired.

13. A method for initializing an aerosol generator, the method comprising:
    providing an aerosolization device comprising a housing having a mouthpiece, an aerosol generator disposed in the housing, a flow sensor, and a controller to control operation of the aerosol generator;
    inhaling an initial tidal breath through the mouthpiece to produce a flow of air through the mouthpiece;
    sensing the flow of air with the flow sensor;
    measuring and storing in the controller an initialization time period where the inhaled breath exceeds a threshold flow rate; and
    calculating an aerosol generator operation time period that is equal to the initialization time period minus a stored value in the controller that is an estimate of a time period to move substantially all of an aerosol produced from the aerosol generator through a dead space volume with generally aerosol free chase air from a tidal breath, wherein the dead space is a volume between the mouthpiece and the entrance to the lungs.

14. A method as in claim 13, wherein the initial tidal breath begins at a time T0, and further comprising sensing with the sensor at a time T1 when the flow produced by the inhaled breath exceeds the threshold flow rate, and a time T3 when the flow produced by the inhaled breath falls below the threshold flow rate, and wherein the initialization time period is equal to T3 minus T1.

15. A method as in claim 13, wherein the threshold flow rate is about 8 liters per minute.

16. A method as in claim 13, further comprising storing the operation time period in a random access memory of the controller.

17. A method as in claim 13, wherein the dead space volume is in the range from about 200 cubic centimeters to about 400 cubic centimeters.

18. A method as in claim 13, further comprising supplying a liquid to the aerosol generator prior to operation of the aerosol generator.

19. A method as in claim 13, wherein the dead space volume is in the range from about 200 cubic centimeters to about 400 cubic centimeters.

20. A method as in claim 13, further comprising supplying a liquid to the aerosol generator prior to operation of the aerosol generator.

21. An aerosolization device comprising:

a housing having a mouthpiece;

an aerosol generator disposed in the housing;

a flow sensor; and a controller to control operation of the aerosol generator;

a memory accessible by the controller; and a look up table accessible by the controller;

wherein the controller is configured to stop operation of the aerosol generator based at least in part on information in the look up table, wherein the look up table comprises a table of values that represent the time during which an inspiratory flow would fill the effective dead space based on breathing criteria and anatomic estimates according to a patient's individual statistics.

22. An aerosolization device comprising:

a housing having a mouthpiece;

an aerosol generator disposed in the housing;

a flow sensor; and a controller to control operation of the aerosol generator;

wherein the controller is configured to begin operation of the aerosol generator upon receipt of a signal from the flow sensor indicating that a threshold flow rate has been achieved by a user when inhaling through the mouthpiece and to stop operation of the aerosol generator after passage of an operation time period that is selected such that continuation of the breath delivers substantially all of the produced aerosol to the user's lungs, and wherein the controller is configured to calculate and store an initialization time period that is equal to the length of time that the flow rate is above the threshold flow rate during an initialization process, and wherein the controller is further configured to calculate the operation time period by subtracting the stored value from the initialization time period.

* * * * *